(12) United States Patent  
Ohta et al.

(10) Patent No.: US 7,924,980 B2
(45) Date of Patent: Apr. 12, 2011

(54) PORTABLE RADIATION IMAGE CONVERTING DEVICE

(75) Inventors: Yasunori Ohta, Ashigarakami-gun (JP); Naoyuki Nishino, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 139 days.

(21) Appl. No.: 12/379,494

(22) Filed: Feb. 24, 2009

(65) Prior Publication Data

US 2009/0220052 A1    Sep. 3, 2009

(30) Foreign Application Priority Data

Feb. 29, 2008  (JP) ................................. 2008-050024

(51) Int. Cl.
*H05G 1/64*  (2006.01)

(52) U.S. Cl. .................................. 378/98.8; 250/370.09

(58) Field of Classification Search .................... 378/98, 378/98.3, 98.5, 98.8; 250/370.09
See application file for complete search history.

(56) References Cited

U.S. PATENT DOCUMENTS

| 6,344,652 | B1 * | 2/2002 | Shoji .......................... 250/370.09 |
| 6,554,472 | B1 * | 4/2003 | Dietz et al. ..................... 378/197 |
| 6,738,531 | B1 * | 5/2004 | Funahashi ...................... 382/294 |
| 6,860,609 | B2 * | 3/2005 | Olson et al. .................... 353/122 |
| 6,966,651 | B2 * | 11/2005 | Johnson .......................... 353/15 |
| 6,999,121 | B2 * | 2/2006 | Endo ............................. 348/297 |
| 7,109,491 | B2 * | 9/2006 | Shinden ..................... 250/370.09 |
| 7,203,278 | B2 * | 4/2007 | Wendt et al. ................... 378/98.8 |
| 7,247,859 | B2 * | 7/2007 | Murphy et al. ........... 250/370.09 |
| 7,250,608 | B2 * | 7/2007 | Ozeki ....................... 250/370.08 |
| 7,508,915 | B2 * | 3/2009 | Amitani et al. ............... 378/98.8 |
| 7,545,914 | B2 * | 6/2009 | Kito et al. ..................... 378/98.8 |
| 7,573,034 | B2 * | 8/2009 | Heath et al. ............... 250/361 R |

FOREIGN PATENT DOCUMENTS

| JP | A 2000-131785 | 5/2000 |
| JP | A 2004-97635 | 4/2004 |

* cited by examiner

*Primary Examiner* — Allen C. Ho
(74) *Attorney, Agent, or Firm* — Solaris Intellectual Property Group, PLLC (57) ABSTRACT

A portable radiation image converting device has: an image data generating unit that is sensitive to radiation, and that generates image data expressing a radiation image manifested by radiation that is transmitted through a subject and is irradiated onto an image-receiving surface; a storage unit storing image data generated by the image data generating unit; and one or more projecting units projecting, to a device exterior, various types of information including a radiation image expressed by image data that is stored in the storage unit. Various types of information including a radiation image that is generated by radiation, that has been transmitted through a subject and irradiated onto an image-receiving surface, and is stored in a memory, are projected to a device exterior by a projecting device. A portable radiation image converting device at which confirmation of a stored radiation image is easy to carry out is thereby provided.

8 Claims, 6 Drawing Sheets

PORTABLE RADIATION IMAGE CONVERTING DEVICE

CROSS-REFERENCE TO RELATED APPLICATIONS

This application claims priority under 35 USC 119 from Japanese Patent Application No. 2008-050024, the disclosure of which is incorporated by reference herein.

BACKGROUND OF THE INVENTION

1. Field of the Invention

The present invention relates to a portable radiation image converting device, and in particular, relates to a portable radiation image converting device that generates image data expressing a radiation image that is manifested by irradiated radiation, and stores the generated image data.

2. Description of the Related Art

FPDs (flat panel detectors), in which an X-ray sensitive layer is disposed on a TFT (thin film transistor) active matrix substrate and that can convert X-rays directly into digital data, have been put into practical use in recent years. Further, portable radiation image converting devices (hereinafter also called "electronic cassettes"), that generate image data expressing a radiation image that is manifested by radiation irradiated by using an FPD or the like and that store the generated image data, have been put into practical use.

Because the electronic cassette is portable, a patient can be photographed as is while on a stretcher or on a bed, and the place to be photographed can be adjusted by changing the position of the electronic cassette. Therefore, electronic cassettes can flexibly handle even patients who are unable to move.

As a technique for confirming a radiation image stored in such an electronic cassette, Japanese Patent Application Laid-Open (JP-A) No. 2000-131785 discloses a technique of providing a display portion at the electronic cassette itself and displaying a radiation image on the display portion, and a technique of providing a removable display portion separately from the electronic cassette, connecting the electronic cassette and the display portion, and displaying a radiation image.

Further, JP-A No. 2004-97635 discloses a technique of removably providing a display portion via plural arms at one side surface of an electronic cassette. At the time of photographing, the arms are removed from the electronic cassette. After photographing is completed, the arms are connected to the cassette, and the photographed radiation image is displayed on the display portion.

However, in the technique disclosed in JP-A No. 2000-131785, if the display portion is provided at the electronic cassette itself, there are cases in which the display portion overlaps the patient. Or, if the display portion is made to be small so as to not overlap the patient, it is difficult to confirm the radiation image. Further, if a removable display portion is provided separately from the electronic cassette, the position at which the unit, that includes the display portion, can be connected to the electronic cassette is decided. Therefore, in cases in which the direction in which the electronic cassette is set is changed in accordance with the affected part of the patient, the position of the display portion moves, and it is difficult to confirm the radiation image at the display portion. Further, because the display portion must be carried separately from the electronic cassette, there is the problem that it is troublesome.

In the technique disclosed in JP-A No. 2004-97635, the display portion is provided via plural (two) arms such that the orientation thereof can be changed to a desired direction. However, the changeable orientation of the display portion is limited by the two arms, and there are cases in which it is difficult to change the orientation well to the desired direction, and cases in which confirmation of the radiation image is difficult. Moreover, increasing the number of arms in order to improve the viewability at the display portion is considered, but there is the problem that the structure of the arm becomes complex.

SUMMARY OF THE INVENTION

The present invention was developed in consideration of the above-described circumstances, and provides a portable radiation image converting device at which it is easy to confirm a stored radiation image.

A portable radiation image converting device relating to a first aspect of the present invention includes: an image data generating unit that is sensitive to radiation, and that generates image data expressing a radiation image manifested by radiation that is transmitted through a subject and is irradiated onto an image-receiving surface; a storage unit storing image data generated by the image data generating unit; and one or more projecting units projecting, to a device exterior, various types of information including a radiation image expressed by image data that is stored in the storage unit.

In the portable radiation image converting device of the first aspect of the present invention, image data, that expresses a radiation image manifested by radiation that is transmitted through a subject and is irradiated onto an image-receiving surface, is generated by an image data generating unit that is sensitive to radiation. The image data generated by the image data generating unit is stored in the storage unit.

Further, in the first aspect of the present invention, various types of information, including a radiation image expressed by image data that is stored in the storage unit, are projected to the device exterior by the one or more projecting units.

In this way, in accordance with the portable radiation image converting device of the first aspect of the present invention, various types of information, including a radiation image stored in the storage unit, are projected to the device exterior by the projecting unit, and therefore, confirmation of a stored radiation image is easy to carry out.

Note that it is preferable that the projecting unit of the first aspect of the present invention be provided at a side surface of a housing.

Further, in the portable radiation image converting device of the first aspect of the present invention, a plurality of the projecting units may be provided at respectively different side surfaces of the housing, and the portable radiation image converting device may further have a receiving section that receives an instruction selecting the projecting unit that projects various types of information.

The portable radiation image converting device of the first aspect of the present invention may further have a distance measuring unit that measures a distance in a projecting direction in which the projecting unit projects various types of information, wherein a start of projecting by the projecting unit is triggered by a change in a distance measured by the distance measuring unit.

Moreover, the portable radiation image converting device of the first aspect of the present invention may further have: a distance measuring unit measuring a distance in a projecting direction in which the projecting unit projects various types of information; and a projected light amount control unit carrying out control that changes a projected light amount that is projected from the projecting unit, in accordance with a distance measured by the distance measuring unit.

In the portable radiation image converting device of the first aspect of the present invention, the projecting unit may change contents of information that are projected before and after photographing of a radiation image in which the radiation is irradiated onto the image-receiving surface.

The portable radiation image converting device of the first aspect of the present invention may further have an image processing unit that carries out image processing that reverses left and right of a radiation image expressed by the image data, so as to switch a front surface and a reverse surface of a radiation image projected by the projecting unit.

In the portable radiation image converting device of the first aspect of the present invention, it is preferable that a projecting section of the projecting unit, which projecting section projects information to the device exterior, is movable, and a projecting direction can be changed.

As described above, the portable radiation image converting device of the first aspect of the present invention has the excellent effect that, because various types of information, including a radiation image that is stored in the storage unit, are projected to the device exterior by the projecting unit, confirmation of a stored radiation image is easy to carry out.

DETAILED DESCRIPTION OF THE INVENTION

An example of an exemplary embodiment of the present invention will be described in detail hereinafter with reference to the drawings.

Figure 1:
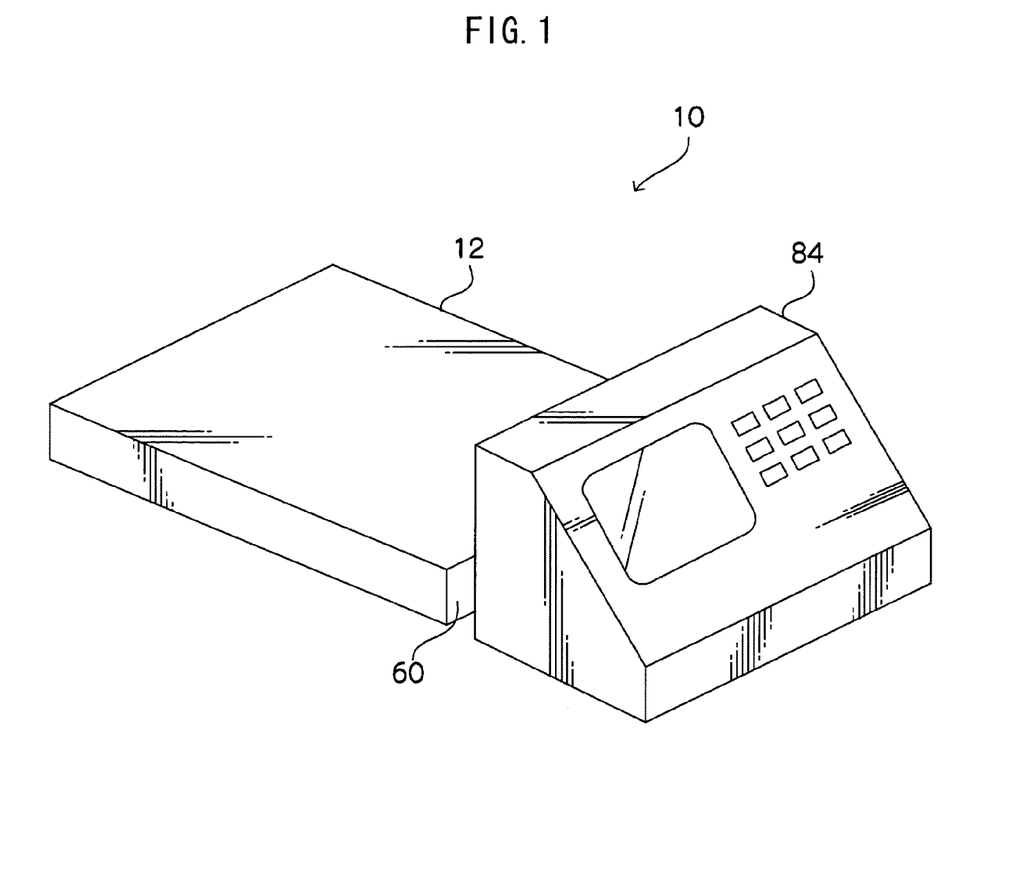
FIG. 1 is a drawing showing the schematic structure of an electronic cassette relating to an exemplary embodiment and an image read-out device.

A radiation image handling system 10, that is equipped with an electronic cassette 12 relating to the present exemplary embodiment, is shown in FIG. 1.

The radiation image handling system 10 is portable, and is structured from an electronic cassette 12 and an image read-out device 84. Each time that radiation that carries image information is irradiated, the electronic cassette 12 generates image data expressing that image information, and can accumulate and store the image data. The image read-out device 84 can read-out the image data that is accumulated and stored in the electronic cassette 12.

Figure 2A:
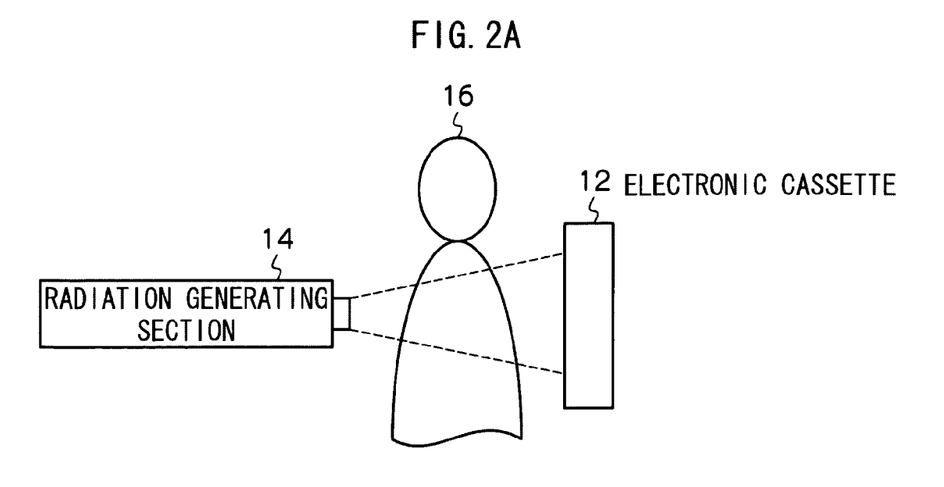
FIG. 2A is a schematic drawing showing the arrangement of the electronic cassette at the time of radiation image photographing.

As shown in FIG. 2A, at the time of photographing a radiation image, the electronic cassette 12 is disposed such that there is a space between the electronic cassette 12 and a radiation generating section 14 that generates radiation such as X-rays or the like. The region between the radiation generating section 14 and the electronic cassette 12 at this time is a photographing position at which a subject 16 is positioned. When photographing of a radiation image is instructed, the radiation generating section 14 emits radiation of a radiation amount that corresponds to photographing conditions and the like that are provided in advance. Due to the radiation that is emitted from the radiation generating section 14 being transmitted through the subject 16 who is positioned at the photographing position, the radiation carries image information, and thereafter, is irradiated onto the electronic cassette 12.

Figure 2B:
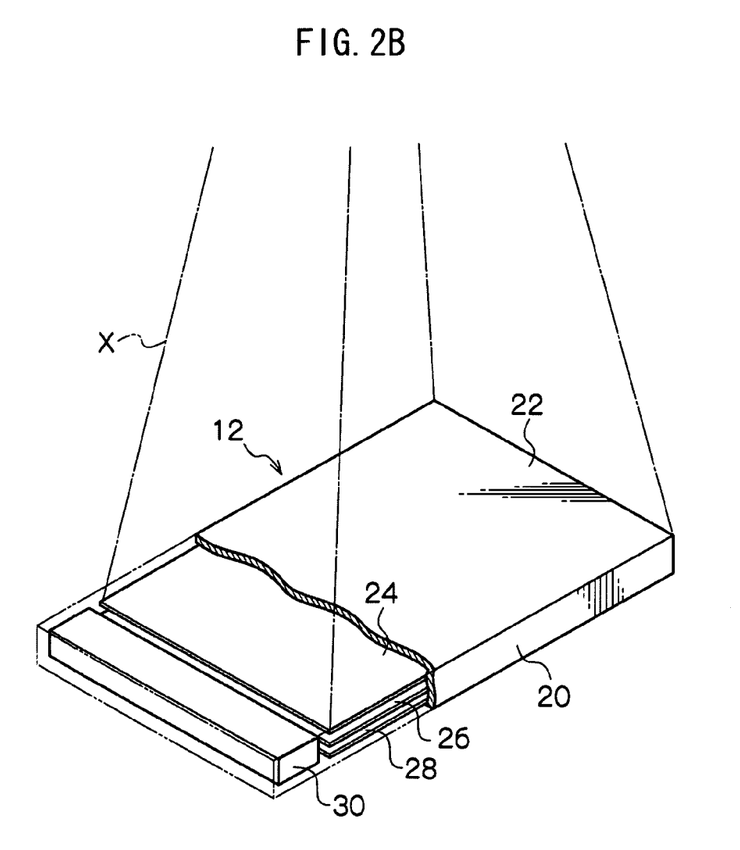
FIG. 2B is a perspective view showing the internal structure of the electronic cassette.

As shown in FIG. 2B, the electronic cassette 12 is covered by a flat-plate-shaped casing (housing) 20 that is formed of a material and to a thickness such that radiation X can be transmitted therethrough. A grid 24 that removes scattered radiation of the radiation X that arises as the radiation is transmitted through the subject 16, a radiation detector (radiation detecting panel) 26 that detects the radiation X, and a lead plate 28 that absorbs the back-scattered radiation of the radiation X, are disposed at the interior of the casing 20 in that order from an irradiation surface 22 side of the casing 20 at which the radiation X is irradiated. Note that the irradiation surface 22 of the casing 20 may be structured by the grid 24. Further, a case 30, that houses various types of circuits (that will be described later) including microcomputers, is disposed at one end side of the interior of the casing 20. In order to avoid damage, that accompanies irradiation of the radiation X, to the various types of circuits that are housed at the interior of the case 30, it is desirable to provide a lead plate or the like at the irradiation surface 22 side of the case 30.

Figure 3:
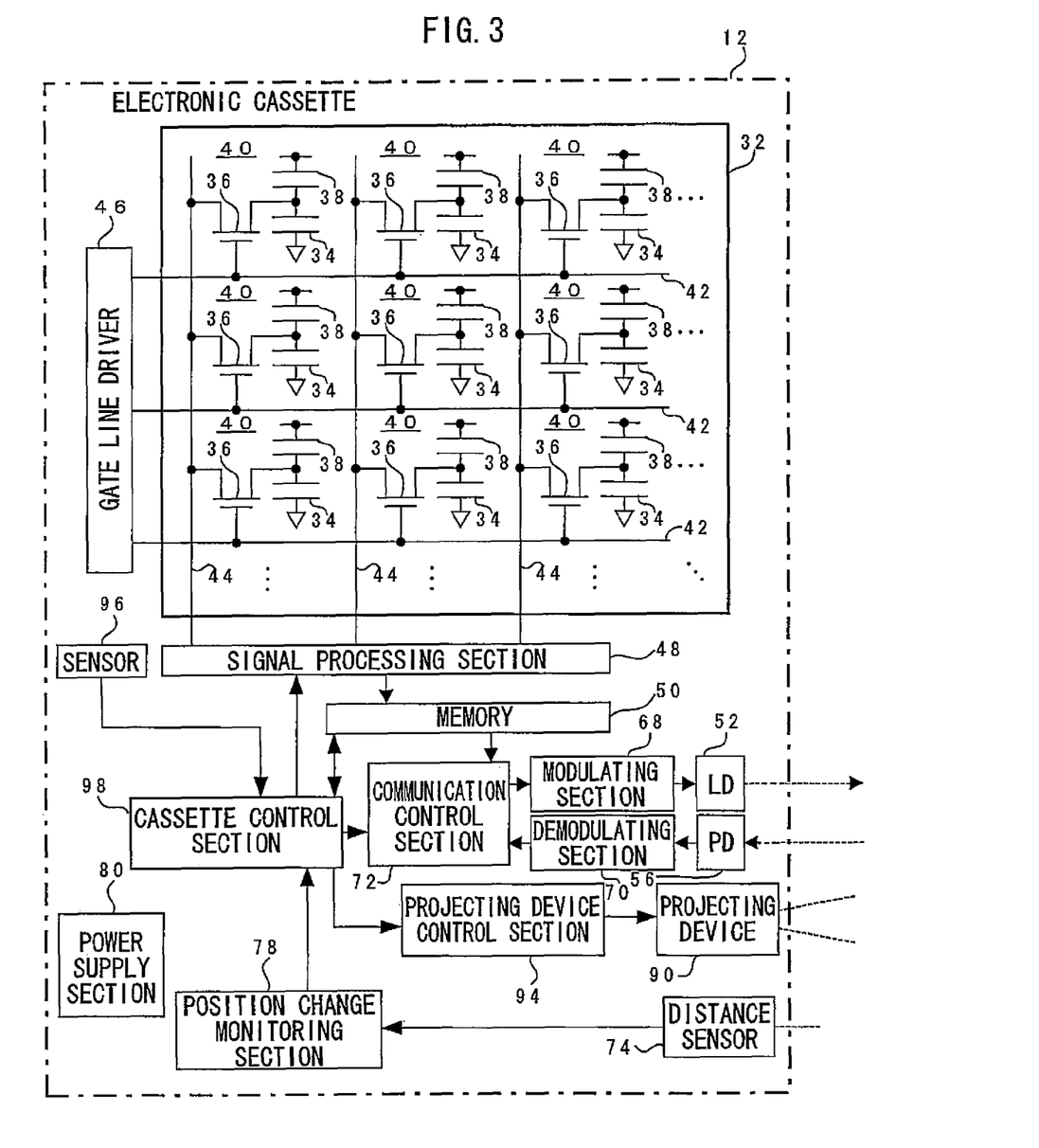
FIG. 3 is a block diagram showing the detailed structure of the electronic cassette relating to the exemplary embodiment.

The detailed structure of the electronic cassette 12 relating to the present exemplary embodiment is shown in FIG. 3.

The radiation detector 26 of the electronic cassette 12 is structured such that a photoelectric converting layer, that absorbs radiation and converts it into charges, is layered on a TFT active matrix substrate 32. The photoelectric converting layer is formed from, for example, an amorphous a-Se (amorphous selenium) whose main component is selenium (e.g., a content of greater than or equal to 50%). When radiation is irradiated, the photoelectric converting layer generates, at the interior thereof, charges (electron-hole pairs) of a charge amount corresponding to the irradiated radiation amount, and thereby converts the irradiated radiation into charges. Further, numerous pixel portions 40 are arranged in the form of a matrix on the TFT active matrix substrate 32. (In FIG. 3, the photoelectric converting layer corresponding to the individual pixel portions 40 is shown schematically as photoelectric converting portions 38.) The pixel portion 40 has an accumulating capacitor 34 that accumulates charges generated at the photoelectric converting layer, and a TFT 36 for reading-out the charges accumulated in the accumulating capacitor 34. The charges, that are generated at the photoelectric converting layer accompanying the irradiation of radiation onto the electronic cassette 12, are accumulated in the accumulating capacitors 34 of the individual pixel portions 40. Due thereto, the image information, that is carried by the radiation irradiated on the electronic cassette 12, is converted into charge information and is held at the radiation detector 26.

Plural gate lines 42, that extend in a given direction (the line direction) and are for turning the TFTs 36 of the individual pixel portions 40 on and off, and plural data lines 44, that extend in a direction (the row direction) orthogonal to the gate lines 42 and are for reading-out the accumulated charges from the accumulating capacitors 34 via the TFTs 36 that have been turned on, are provided at the TFT active matrix substrate 32. The individual gate lines 42 are connected to a gate line driver 46, and the individual data lines 44 are connected to a signal processing section 48. When charges are accumulated in the accumulating capacitors 34 of the individual pixel portions 40, the TFTs 36 of the individual pixel portions 40 are turned on in order in units of lines by signals supplied from the gate line driver 46 via the gate lines 42, and the charges, that are accumulated in the accumulating capacitors 34 of the pixel portions 40 whose TFTs 36 have been turned on, are transferred through the data lines 44 as charge signals and are inputted to the signal processing section 48. Accordingly, the charges, that are accumulated in the accumulating capacitors 34 of the individual pixel portions 40, are read-out in order in units of lines.

Although not illustrated, the signal processing section 48 is equipped with an amplifier and a sample holding circuit that are provided for each of the individual data lines 44. The charge signals that are transferred through the individual data lines 44 are amplified at the amplifiers, and thereafter, are held in the sample holding circuits. Further, a multiplexer and an A/D converter are connected in that order to the output sides of the sample holding circuits. The charge signals, that are held in the individual sample holding circuits, are inputted in order (serially) to the multiplexer, and are converted into digital image data by the A/D converter. A memory 50 is connected to the signal processing section 48. The image data, that are outputted from the A/D converter of the signal processing section 48, are stored in order in the memory 50. The memory 50 has a storage capacity that can store image data of plural frames. Each time photographing of a radiation image is carried out, the image data obtained by photographing is successively stored in the memory 50.

Figure 4:
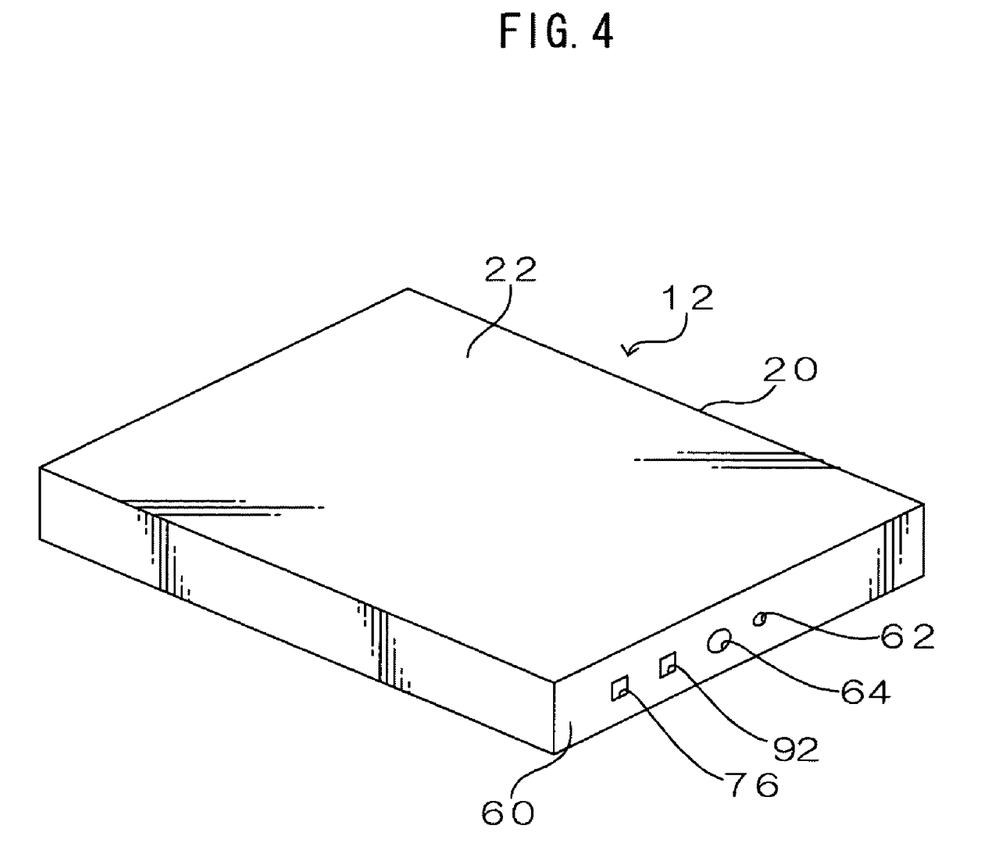
FIG. 4 is a perspective view showing the exterior of the electronic cassette relating to the exemplary embodiment.

The electronic cassette 12 has the function of carrying out wireless communications by laser light with the image read-out device 84, and is equipped with an LD (laser diode) 52 serving as a laser light source, and a PD (photodiode) 56 that detects laser light that is incident from the exterior. In the present exemplary embodiment, as shown in FIG. 4, an exit hole 62 for passage of the laser light exiting from the LD 52, and a light-receiving hole 64 for passage of laser light from the exterior (e.g., the image read-out device 84) are respectively provided in a specific side surface 60 of the casing 20 of the electronic cassette 12. (Because this side surface 60 is disposed so as to oppose the casing of the image read-out device 84 at the time of communicating with the image read-out device 84, this side surface 60 is called the "opposing surface 60" hereinafter.) Note that, in FIG. 1 and FIG. 4, a side surface that contacts a short side of the irradiation surface 22 is used as the opposing surface 60 in which the exit hole 62 and the light-receiving hole 64 are provided. However, the opposing surface 60 is not limited to the same, and may be a side surface that contacts a long side of the irradiation surface 22.

The LD 52 (see FIG. 3) is connected to a communication control section 72 via a modulator 68. The communication control section 72 is connected to the memory 50. The communication control section 72 is realized by a microcomputer. At the time of transmitting information to the image read-out device 84, the communication control section 72 outputs the information that is the object of transmission to the modulator 68. The modulator 68 modulates laser light, that is to exit from the LD 52, by a predetermined modulating method in accordance with the inputted transmission object information, and controls the driving of the LD 52. Laser light, that is modulated in accordance with the transmission object information, is thereby made to exit from the LD 52.

The PD 56 is connected to the communication control section 72 via a demodulating section 70. When laser light from the exterior is received at the PD 56 and a received light amount signal corresponding to the received light amount of the laser light is inputted from the PD 56, the demodulating section 70, on the basis of the received light amount signal that is inputted thereto, demodulates the information that the received laser light carries (the information transmitted from the device that is the communication partner) by a predetermined demodulating method, and outputs the demodulated information to the communication control section 72.

A projecting device 90, that can project various types of information including images to the device exterior, is provided at the electronic cassette 12. In the present exemplary embodiment, a micro projector device such as the DLP (digital light processing) Pico® manufactured by Texas Instruments Incorporated, or the like, is used as the projecting device 90. This DLP Pico® incorporates therein a micro DMD (digital micromirror device), and can project an image by individually driving the respective mirrors that are lined-up two-dimensionally at the DMD. Note that a micro projector device of an LCD system that uses a compact high-temperature poly-silicon (HTPS) TFT liquid crystal panel may be used as the projecting device 90. In the present exemplary embodiment, as shown in FIG. 4, a projection hole 92, that is for passage of the projected light that exits from the projecting device 90, is provided in the opposing surface 60 of the casing 20 of the electronic cassette 12. Note that, in FIG. 4, a side surface that contacts a short side of the irradiation surface 22 is used as the opposing surface 60 in which the projection hole 92 is provided. However, the opposing surface 60 is not limited to the same, and may be a side surface that contacts a long side of the irradiation surface 22.

Figure 5:
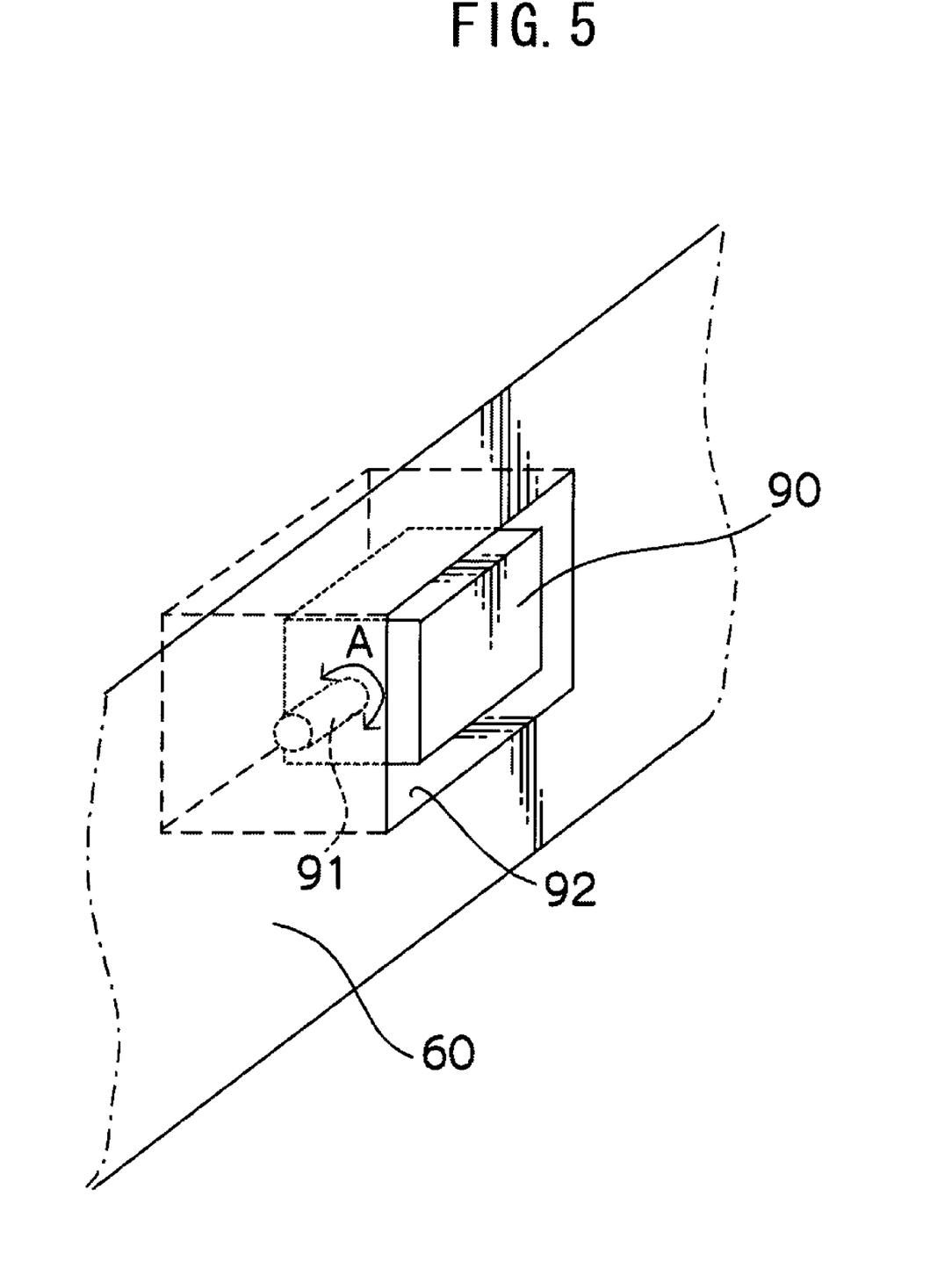
FIG. 5 is a perspective view showing a mechanism that allows the projecting direction of projected light of a projecting device relating to the exemplary embodiment to be changed.

As shown in FIG. 5, the projecting device 90 relating to the present exemplary embodiment is pivotally supported by a shaft 91 that is provided within the projection hole 92 and parallel to the short side of the irradiation surface 22. The projecting direction of the projected light can be changed in the vertical direction due to the projecting device 90 being rotated in the directions of arrow A.

The projecting device 90 (see FIG. 3) is connected to a projecting device control section 94, and is controlled by the projecting device control section 94.

A distance sensor 74 is provided at the electronic cassette 12. In the present exemplary embodiment, as the distance sensor 74, there is used a structure that is provided with a light-emitting element and a light-receiving element, and that measures a time period from after light is emitted from the light-emitting element until the emitted light is reflected by an object and received at the light-receiving element, and that detects the distance to the object on the basis of the measured time period. As shown in FIG. 4, a detection hole 76 is provided in the opposing surface 60 of the casing 20 of the electronic cassette 12. The light emitted from the light-emitting element of the distance sensor 74 passes through the detection hole 76 and is irradiated onto an object that exists in front of the opposing surface 60, and the light reflected at the object passes through the detection hole 76 and is received at the light-receiving element. The distance sensor 74 is connected to a position change monitoring section 78. The position change monitoring section 78 also is realized by a microcomputer. The position change monitoring section 78 monitors changes in the distance detected by the distance sensor 74, or the like. Further, the projecting device control section 94 carries out control to change the projected light amount that is projected from the projecting device 90 in accordance with the distance measured by the distance sensor 74.

A sensor 96 that is sensitive to radiation is provided at the electronic cassette 12, at the side of the radiation detector 26.

The above-described signal processing section 48, memory 50, communication control section 72, projecting device control section 94, position change monitoring section 78, and sensor 96 are connected to a cassette control section 98 that controls the overall operations of the electronic cassette 12. The cassette control section 98 also is realized by a microcomputer. When radiation is detected at the sensor 96, the cassette control section 98 outputs an instruction signal instructing photographing of a radiation image, to the signal processing section 48. Due thereto, the signal processing section 48 reads-out the charges accumulated in the accumulating capacitors 34 of the respective pixel portions 40, and stores the image data in the memory 50.

Further, the electronic cassette 12 relating to the present exemplary embodiment can receive various types of operation instructions in accordance with the number of times the distance detected at the distance sensor 74 changes by greater than or equal to a predetermined value within a predetermined time period (e.g., three seconds) due to, for example, a hand being placed in front of the distance sensor 74. For example, if the distance is changed one time, it is considered that projecting of the radiation image is instructed, and if the distance is changed two times, it is considered that transmitting of the image data to the image read-out device 84 is instructed.

The cassette control section 98 at all times monitors changes in the distance by the position change monitoring section 78. If the distance detected at the distance sensor 74 changes one time by a predetermined value or more during the aforementioned predetermined time period, it is considered that projecting of the radiation image is instructed. The image data stored in the memory 50 is read-out, and, in order for the projecting device 90 to display the entire radiation image expressed by that image data, image processing is carried out in order to decrease the number of pixels of the radiation image by thinning the pixels or by computing average values of plural pixels, and the image data that has undergone the image processing is outputted to the projecting device control section 94. The projecting device control section 94 thereby controls the projecting device 90 on the basis of the inputted image data, and causes the projecting device 90 to project, to the exterior, a radiation image expressed by that image data. Further, if the distance detected at the distance sensor 74 changes twice by a predetermined value or more during the aforementioned predetermined time period, it is considered that transmitting of image data to the image read-out device 84 is instructed, and the cassette control section 98 outputs to the communication control section 72 an instruction signal instructing transmission of the image data. Due thereto, the communication control section 72 reads-out the image data stored in the memory 50, and carries out data transfer processing that transmits that image data to the image read-out device 84.

A power supply section 80 is provided at the electronic cassette 12. The above-described various types of circuits and respective elements (the gate line driver 46, the signal processing section 48, the memory 50, the microcomputers functioning as the communication control section 72 and the position change monitoring section 78 and the cassette control section 98, the modulating section 68, the LD 52, the PD 56, the demodulating section 70, the distance sensor 74, the projecting device 90, the projecting device control section 94, the sensor 96, and the like) are operated by electric power supplied from the power supply section 80. A structure, that incorporates a battery (a rechargeable secondary battery) therein and that supplies electric power from the charged battery to the various circuits and elements, is suitable as the power supply section 80 so that the portability of the electronic cassette 12 is not adversely affected. However, as the battery, a primary battery may be used, or a structure, that is usually connected to a commercial power supply and rectifies and transforms the electric power supplied from the commercial power supply and supplies the electric power to the various circuits and elements, may be used.

Operation of the radiation image handling system 10 relating to the present exemplary embodiment will be described next.

For example, in a case of carrying out photographing of a radiation image of an affected part of a patient who is laying on a bed, at the radiation image handling system 10 relating to the present exemplary embodiment, the electronic cassette 12 is disposed between the bed and the affected part of the patient, and the radiation image generating section 14 is disposed above the bed. In this case, the projecting device 90 of the electronic cassette 12 does not oppose the bed and the patient, and is in a state of being exposed toward the side of the bed. Then, the examining technician operates the radiation image handling system 10, and radiation of a radiation amount, that corresponds to photographing conditions and the like that are provided in advance, exits from the radiation generating section 14.

The radiation that is radiated from the radiation generating section 14 is transmitted through the subject 16, and thereafter, reaches the electronic cassette 12.

Charges, that correspond to the radiation amount of the irradiated radiation, are accumulated in the accumulating capacitors 34 of the respective pixel portions 40 of the radiation detector 26.

When radiation is detected at the sensor 96, the cassette control section 98 outputs, to the signal processing section 48, an instruction signal that instructs photographing of a radiation image. The gate line driver 46 outputs ON signals (+10 to 20 V) to the respective gate lines 42 in order and line-by-line, and turns the respective TFTs 36, that are connected to the respective gate lines 42, on in order and line-by-line. Due thereto, charge signals, that correspond to the charge amounts accumulated in the accumulating capacitors 34 of the respective pixel portions 40, flow-out line-by-line to the respective data lines 44, and, after being amplified at the amplifiers, are held at the sample holding circuits. On the basis of the charge signals that flow-out to the data lines 44, the signal processing section 48 detects, as the pixel values of the respective pixels structuring the image, the charge amounts that are accumulated in the respective pixel portions 40. Image information, that expresses the radiation image expressed by the radiation irradiated on the electronic cassette 12, can thereby be obtained. The image data obtained by photographing is stored in the memory 50.

Next, in the case of confirming a photographed radiation image, at the radiation image handling system 10 relating to the present exemplary embodiment, with the position of the electronic cassette 12 being maintained as is, the examining technician, for example, places his/her hand in front of the distance sensor 74 and changes the distance detected at the distance sensor 74 by a predetermined value or more one time during the aforementioned predetermined time period.

When the cassette control section 98 detects that the distance detected at the distance sensor 74 has changed by a predetermined value or more one time during the aforementioned predetermined time period, the cassette control section 98 reads-out the image data stored in the memory 50, carries out image processing on the image data so as to reduce the number of pixels, and outputs the image data, that has been subjected to the image processing, to the projecting device control section 94.

On the basis of the inputted image data, the projecting device control section 94 controls the projecting device 90, and causes the radiation image that is expressed by that image data to be projected to the exterior. Note that, at this time, the projecting device control section 94 controls the projecting device 90 such that, the greater the distance to the object to be projected onto that is measured by the distance sensor 74, the greater the projected light amount, so that the image is displayed appropriately.

Figure 6:
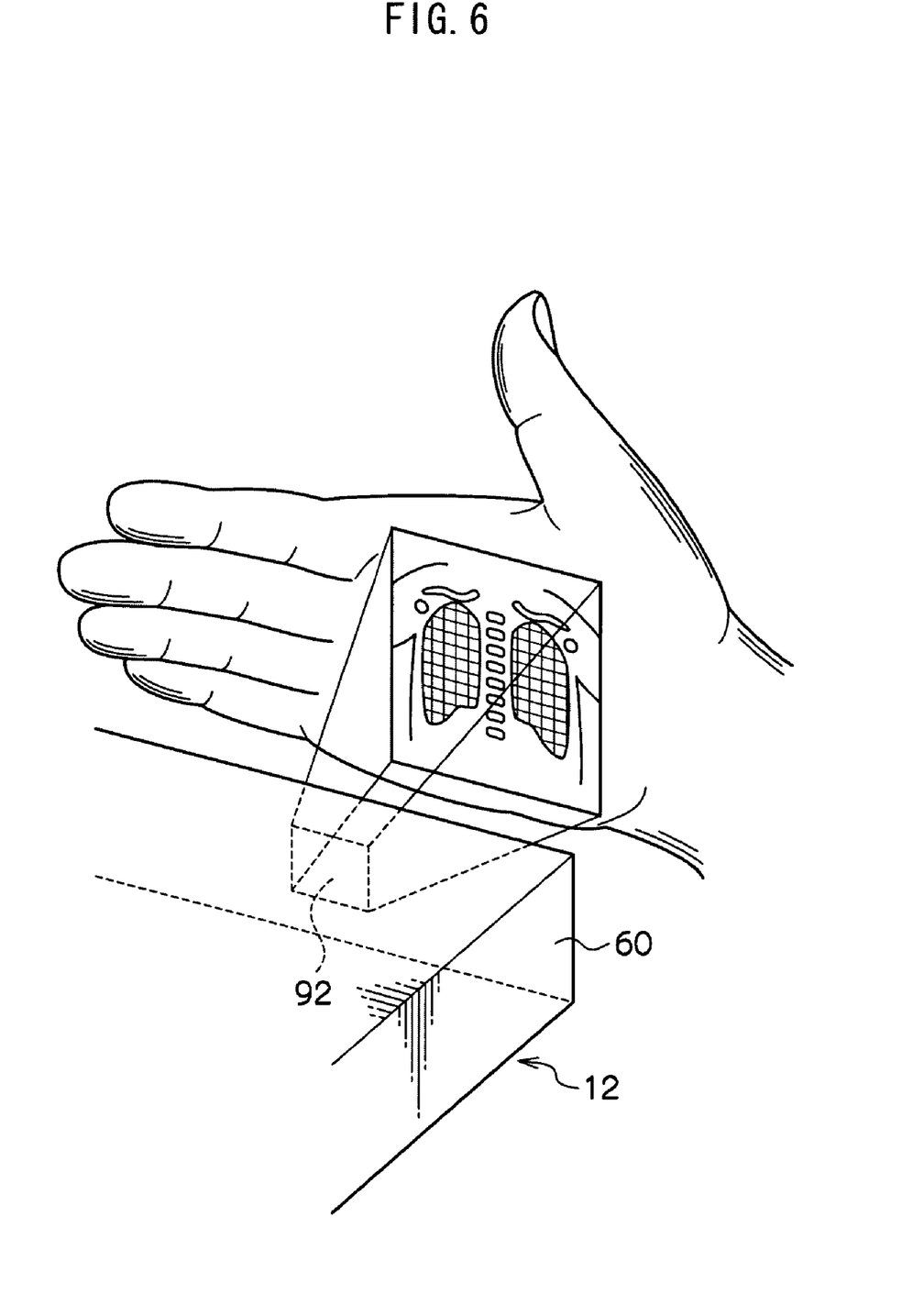
FIG. 6 is a drawing showing an example of results of projecting a radiation image.

The examining technician can confirm the radiation image by causing the projected light, that is made to exit from the projection hole 92 by the projecting device 90, to be projected onto the wall of the room, the palm of a hand, the clothes worn by the technician, a bed sheet, or the like. At this time, at the projecting device 90, the projecting direction of the projected light can be changed up and down as shown in FIG. 5, and therefore, the projecting direction can be changed so that it is easy to visually recognize the radiation image. A case in which the projected light is projected onto the palm of a hand is shown in FIG. 6.

In this way, at the electronic cassette 12 relating to the present exemplary embodiment, at the time of confirming a radiation image, the patient does not have to be moved and can remain laying in bed, and there is no need to place the electronic cassette 12 near and take it away from the affected part. Further, also at times when it is judged, as a result of confirming the radiation image, that photographing must be carried out again (e.g., at times when the patient moves and blurring arises, or at times when the positioning is incorrect and the necessary region is not photographed), photographing can be carried out again in that state as is by adjusting the position of the electronic cassette 12.

The front surface and the reverse surface of the projected radiation image are reversed, and there are cases in which it is difficult to confirm the radiation image. Thus, in cases in which the cassette control section 98 detects that the distance detected at the distance sensor 74 has changed by greater than or equal to a predetermined value during the projecting of a radiation image, the cassette control section 98 may carry out switching of the front surface and the reverse surface of the radiation image projected by projecting device 90, by carrying out image processing for reversing the left and right of the radiation image.

Next, when image data stored in the electronic cassette 12 is to be transmitted to the image read-out device 84, at the radiation image handling system 10 relating to the present exemplary embodiment, the examining technician places the electronic cassette 12 such that the opposing surface 60 faces the opposing surface of the image read-out device 84. Then, the examining technician, for example, places his/her hand in front of the distance sensor 74, and twice changes, by a predetermined value or more during the aforementioned predetermined time period, the distance detected at the distance sensor 74.

When the cassette control section 98 detects that the distance detected at the distance sensor 74 has changed by a predetermined value or more twice during the aforementioned predetermined time period, the cassette control section 98 outputs, to the communication control section 72, an instruction signal instructing transmission of image data.

Via the modulating section 68, the communication control section 72 causes laser light to exit from the LD 52, and transmits predetermined information by laser light from its own device (modulates, in accordance with predetermined information, laser light that is to exit from the LD of its own device), and confirms the contents of information received by laser light from the partner device (information obtained by demodulating the laser light that exited from the LD of the partner device and was received at the PD of its own device). The communication control section 72 thereby carries out partner device confirmation processing that confirms whether or not the partner device is a proper device. Note that information, such as cassette IDs for identifying the individual electronic cassettes 12, or the like is an example of the information that the electronic cassette 12 transmits to the image read-out device 84. Information, that expresses that the device itself is an image read-out device, or the like is an example of the information that the image read-out device 84 transmits to the electronic cassette 12.

If the communication control section 72 judges that the partner device is a proper device (the image read-out device 84), the communication control section 72 reads-out image data from the memory 50, and transmits that image data to the partner device (the image read-out device 84) by laser light.

As described above, in accordance with the present exemplary embodiment, various types of information, including a radiation image that is generated by radiation that has been transmitted through a subject and irradiated on the image-receiving surface and that is stored in the memory 50, are projected by the projecting device 90 to the device exterior. Therefore, confirmation of a stored radiation image is easy to carry out.

Moreover, in accordance with the present exemplary embodiment, because there is no need to provide a display portion at the electronic cassette 12 itself, the proportion of the region at which a radiation image can be photographed of the image-receiving surface (the region at which the radiation detector 26 can be disposed) can be made to be large.

Still further, in accordance with the present exemplary embodiment, because there is no need to carry a display portion separately, the radiation image can be confirmed easily.

Note that the present exemplary embodiment describes cases in which various types of operation instructions are inputted in accordance with the number of times that the distance detected at the distance sensor 74 changes by a predetermined value or more during a predetermined time period. However, the present invention is not limited to the same. For example, various types of operation instructions may be inputted in accordance with the changed distance. Further, an operation panel may be provided at the electronic cassette 12, and various types of operation instructions may be inputted from this operation panel, and the cassette control section 98 may receive the various types of operation instructions from the operation panel.

The present exemplary embodiment describes a case in which the one projecting device 90 is provided at one side surface of the electronic cassette 12, but the present invention is not limited to the same. For example, one of the projecting devices 90 may be provided at each of the side surfaces of the electronic cassette 12. In this case, the cassette control section 98 may switch the projecting device 90 that projects the radiation image in accordance with the number of times the distance detected at the distance sensor 74 changes, or in accordance with an operation instruction from an operation panel.

Further, the present exemplary embodiment describes a case in which the projecting direction of the projected light of the projecting device 90 can be changed up and down due to the projecting device 90 being pivotally supported by the shaft 91 that is provided within the projection hole 92 in parallel to the short side of the irradiation surface 22. However, the present invention is not limited to the same. For example, the projecting direction of the projected light of the projecting device 90 can be changed in up, down, left and right directions by a member, that pivotally supports the projecting device 90 by the shaft 91, being pivotally supported by a shaft that is provided in the up-down direction.

Moreover, although the present exemplary embodiment describes a case in which the electronic cassette 12 and the image read-out device 84 carry out wireless communications by laser light, the present invention is not limited to the same. Wireless communications may be carried out, for example, by using infrared rays. Or, wireless communications may be carried out by a wireless LAN or Bluetooth or the like. Further, the electronic cassette 12 and the image read-out device 84 may be connected by a communications cable or the like, and the reception and transmission of various types of data may be carried out thereby.

The image that is projected before and after photographing of the radiation image may be changed. For example, before a radiation image is photographed, the remaining capacity of the memory 50 may be projected, and, after the radiation image is photographed, the photographed radiation image may be projected. The state of usage of the memory 50 can thereby be confirmed easily. Further, the image that is projected can be switched by an operation panel or in accordance with the number of times the distance detected at the distance sensor 74 is changed.

Moreover, a warning or the like, that expresses that the remaining amount of the memory 50 has become less than, for example, the data amount of the image data of one image (frame), may be projected.

Information relating to the photographing of the radiation image, e.g., identifying information structured from information such as an ID number, name, date of birth, sex, region of photographing, photographing time/date, or the like, may be received from the image read-out device 84 in advance and stored in the memory 50, and the identifying information may be projected successively each time photographing of a radiation image is carried out. For example, in a case in which a predetermined operation expressing that confirmation of the radiation image has been completed is carried out, if the information that is projected is made to be identifying information of the person who is to be photographed next, the photographing of radiation images can be carried out efficiently. Note that all of the identifying information may be successively displayed, or some of the identifying information may be projected successively.

By also storing, in the memory 50, photographing conditions as information relating to photographing of a radiation image and projecting the photographing conditions, photographing can be carried out under the correct photographing conditions. Further, if obtained image data is stored in the memory 50 in correspondence with identifying information or photographing conditions, management of the image data can be facilitated by using the identifying information or the like. Note that, if a data protecting means for prohibiting the rewriting and deleting of image data is provided at the memory 50, the image data and the like that are stored in the memory 50 can be protected due to the rewriting and deleting of the image data and the like being prohibited by the data protecting means after photographing is finished.

In addition, the structure of the radiation image handling system 10 (see FIG. 1) and the structure of the electronic cassette 12 (see FIG. 2A through FIG. 5) that were described in the present exemplary embodiment are examples, and appropriate changes may of course be made thereto within a scope that does not deviate from the gist of the present invention.

The radiation detector 26 included in the electronic cassette 12 in the radiation image handling system according to the present exemplary embodiments is a detector that directly converts radiation X incident thereon by a photoelectrical conversion layer (not shown), but it is not limited thereto, and a so-called indirect type radiation detector may also be used in which radiation X incident thereon is converted to visible light by a scintillator and then the visible light is converted to an electrical signal using amorphous silicon (a-Si) or the like as described, for example, in Japanese Patent No. 3494683.

Further, the radiation detector 26 is a so-called TFT read-out type radiation detector in which a charge signal is read out by TFT, but it is not limited thereto, and so-called optical read-out type radiation detector may also be used in which a stored charge signal is read out by irradiating read-out light as described, for example, in Japanese Patent Laid-Open No. 2000-105297.

What is claimed is:

1. A portable radiation image converting device comprising:
    an image data generating unit that is sensitive to radiation, and that generates image data expressing a radiation image manifested by radiation that is transmitted through a subject and is irradiated onto an image-receiving surface;
    a storage unit storing image data generated by the image data generating unit; and
    a projecting unit that projects, to a device exterior, various types of information including a radiation image expressed by image data that is stored in the storage unit.

2. The portable radiation image converting device of claim 1, further comprising a housing, wherein the projecting unit is provided at a side surface of the housing.

3. The portable radiation image converting device of claim 2, further comprising one or more additional projecting units, wherein all projecting units in the portable radiation image converting device are provided at respectively different side surfaces of the housing, and the portable radiation image converting device further comprises a receiving section that receives an instruction selecting the projecting unit that projects various types of information.

4. The portable radiation image converting device of claim 1, further comprising a distance measuring unit that measures a distance in a projecting direction in which the projecting unit projects various types of information, wherein a start of projecting by the projecting unit is triggered by a change in a distance measured by the distance measuring unit.

5. The portable radiation image converting device of claim 1, further comprising:
    a distance measuring unit measuring a distance in a projecting direction in which the projecting unit projects various types of information; and
    a projected light amount control unit carrying out control that changes a projected light amount that is projected from the projecting unit, in accordance with a distance measured by the distance measuring unit.

6. The portable radiation image converting device of claim 1, wherein the projecting unit changes contents of information that are projected before and after photographing of a radiation image in which the radiation is irradiated onto the image-receiving surface.

7. The portable radiation image converting device of claim 1, further comprising an image processing unit that carries out image processing that reverses left and right of a radiation image expressed by the image data, so as to switch a front surface and a reverse surface of a radiation image projected by the projecting unit.

8. The portable radiation image converting device of claim 1, wherein a projecting section of the projecting unit, which projecting section projects information to the device exterior, is movable, and a projecting direction can be changed.

* * * * *